United States Patent
Tanizaki et al.

(10) Patent No.: US 7,202,391 B2
(45) Date of Patent: Apr. 10, 2007

(54) PROCESS FOR INHIBITING POLYMERIZATION OF AN AROMATIC VINYL COMPOUND

(75) Inventors: Seiji Tanizaki, Mie (JP); Junichi Nakajima, Mie (JP)

(73) Assignee: Hakuto Co., Ltd., Tokyo (JP)

( * ) Notice: Subject to any disclaimer, the term of this patent is extended or adjusted under 35 U.S.C. 154(b) by 439 days.

(21) Appl. No.: 10/476,140

(22) PCT Filed: Apr. 18, 2002

(86) PCT No.: PCT/JP02/03871

§ 371 (c)(1),
(2), (4) Date: Oct. 24, 2003

(87) PCT Pub. No.: WO02/088054

PCT Pub. Date: Nov. 7, 2002

(65) Prior Publication Data

US 2004/0147797 A1 Jul. 29, 2004

(30) Foreign Application Priority Data

Apr. 25, 2001 (JP) ............................. 2001-128281
Apr. 5, 2002 (JP) ............................. 2002-103895

(51) Int. Cl.
*C10G 7/00* (2006.01)
*C10G 9/16* (2006.01)

(52) U.S. Cl. ...................... 585/950; 585/832; 585/856; 585/857; 585/858; 585/859; 585/860; 585/863; 208/47; 208/48; 208/181; 208/255; 208/256

(58) Field of Classification Search ................ 585/950, 585/832, 856–860, 863; 208/47, 48, 181, 208/255, 256
See application file for complete search history.

(56) References Cited

U.S. PATENT DOCUMENTS

| 5,312,952 A | 5/1994 | Grossi et al. |
| 5,540,861 A | 7/1996 | Grossi et al. |
| 5,824,829 A | 10/1998 | Maeda et al. |

FOREIGN PATENT DOCUMENTS

| JP | 49-81326 | 8/1974 |
| JP | 63-316745 | 12/1988 |
| JP | 8-34748 | 2/1996 |

*Primary Examiner*—Tam M. Nguyen
(74) *Attorney, Agent, or Firm*—Flynn, Thiel, Boutell & Tanis, P.C.

(57) ABSTRACT

According to the present invention, there is provided a process for inhibiting the polymerization of an aromatic vinyl compound which is capable of efficiently inhibiting the polymerization of an aromatic vinyl compound not only in an initial stage but also over a long term in the stage of producing, purifying, storing or transporting the aromatic vinyl compound, and which is excellent in handling. The present invention relates to a process for inhibiting the polymerization of an aromatic vinyl compound which requires the step of adding a 2-nitrophenol compound in combination with a sulfonic acid compound to the aromatic vinyl monomer during the stage of producing, purifying, storing or transporting the aromatic vinyl compound.

5 Claims, 1 Drawing Sheet

PROCESS FOR INHIBITING POLYMERIZATION OF AN AROMATIC VINYL COMPOUND

TECHNICAL FIELD

The present invention relates to a process for inhibiting polymerization of an aromatic vinyl compound or of a process fluid containing it during the stage of producing, purifying, storing or transporting it.

BACKGROUND ART

Among aromatic vinyl compounds, styrene especially is an industrially very important compound as a raw material for preparing polystyrene, a synthetic rubber, an ABS resin, etc. and has been industrially manufactured in a large amount.

In general, an aromatic vinyl compound is extremely susceptible to polymerization so that it easily undergoes polymerization under the influence of the heat generated during its preparation or purification step, thereby causing a lowering in the yield of the monomeric aromatic vinyl compound and, further, the formation of fouling in the facilities involved to induce trouble in operating the facilities. As the countermeasure taken hitherto, a process wherein a certain polymerization inhibitor is added to the process fluid containing an aromatic vinyl compound has been proposed and practically carried out. For example, there have been proposed a process employing phenols, nitrosophenols and/or nitrophenols (Japanese Patent Application Laid-Open No. Sho 63-316745), one employing piperidine-1-oxyls (Japanese Patent Application Laid-Open No. Hei 1-165534), one employing nitrophenols together with piperidineoxyls (Japanese Patent Application Laid-Open No. Hei 6-166636), one employing an alkylsulfonic acid and dialkylhydroxylamine in combination (U.S. Pat. No. 4,654,450 specification), one employing phosphoric acid ester and an alkylsulfonic acid in combination (U.S. Pat. No. 4,425,223 specification), one adding phenol-, amine- and/or nitroso-related polymerization inhibitors together with a sulfonic acid compound such as dodecyl-benzene-sulfonic acid or the like and its salt in order to suppress an increase in viscosity in an olefin preparation process (Japanese Patent Application Laid-Open No. Hei 7-166152), and one adding a quinone-, hydroquinone- or nitroso-related polymerization inhibitor, or an amine-related polymerization inhibitor such as phenylenediamine together with a sulfonic acid compound such as dodecylbenzene-sulfonic acid or the like and its salt for preventing formation of fouling in step treating a vinyl compound (Japanese Patent Application Laid-Open No. Hei 8-34748). Among them, especially 2,4-dinitrophenol (DNP) and 2,4-dinitro-6-methylphenol, 2,4-dinitro-6-sec-butylphenol (DNBP) which are nitrophenol compounds have been often used as the polymerization inhibitors for the aromatic vinyl compound. However, these chemical agents have a characteristic property that their inhibitory power toward the polymerization reaction decreases gradually and strict care is needed in handling them because they belong to toxic substances. Accordingly, there has been strongly desired a process which is capable of maintaining a polymerization-inhibiting effect by these chemical agents and reducing the amount of them used.

DISCLOSURE OF THE INVENTION

So, an object of the present invention is to provide a process for inhibiting polymerization of an aromatic vinyl compound in the stage of producing, purifying, storing or transporting the aromatic vinyl compound which is capable of efficiently inhibiting the polymerization not only in an initial stage but also over a long term and which is excellent in handling.

As a result of having in detail studied about the characteristic property based on the polymerization reaction of a vinyl compound, the present inventors have found that by employing a specific nitrophenol compound and sulfonic acid compound in combination, there can be obtained a surprisingly high synergistic action that can be unexpected from the effect obtained when each of them was used singly, and have completed the present invention.

That is, the invention is a process for inhibiting the polymerization of an aromatic vinyl compound which is characterized by adding (A) 2-nitrophenol compound represented by the general formula (I) together with (B) sulfonic acid compound represented by the general formula (II) to said aromatic vinyl compound during the stage of producing, purifying, storing or transporting the aromatic vinyl compound

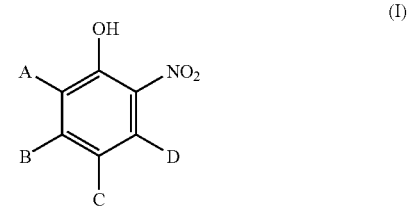

wherein A, B, C and D independently represent hydrogen, a nitro group, a carboxyl group, a hydroxyl group, or a straight or branched chain alkyl group having 1–12 carbon atoms.

wherein R represents a hydroxyl group, a straight or branched chain alkyl group having 1–32 carbon atoms, an alkylphenyl or an alkylnaphthyl group, each having at least one straight or branched chain alkyl group having 1–32 carbon atoms.

The invention also is the process for inhibiting polymerization of an aromatic vinyl compound wherein a 2-nitrophenol compound represented by the general formula (I) is at least one member selected from the group consisting of 2,4-dinitrophenol, 2,6-dinitrophenol, 2,4-dinitro-6-methylphenol, 2,6-dinitro-4-methylphenol, 2,4-dinitro-6-sec-butylphenol and 2,6-dinitro-4-sec-butylphenol.

The invention also is the process for inhibiting polymerization of an aromatic vinyl compound wherein a sulfonic acid compound represented by the general formula (II) is at least one member selected from the group consisting of sulfuric acid, toluenesulfonic acid, xylenesulfonic acid, cumenesulfonic acid, dodecylbenzenesulfonic acid, pentadecylbenzenesulfonic acid and dinonylnaphthalenesulfonic acid.

The invention also is the process for inhibiting polymerization of an aromatic vinyl compound wherein a (A) 2-nitrophenol compound and (B) sulfonic acid compound are added in combination in a proportion of 5:95–95:5 in weight ratio.

The following illustrates the present invention in detail.

Examples of an aromatic vinyl compound whose polymerization is inhibited in the present invention include styrene, substituted styrene (e.g., methylstyrene, ethyl-styrene), divinylbenzene and the like.

The 2-nitrophenol compound of the (A) component which is added for inhibiting polymerization of an aromatic vinyl compound during the stage of producing, purifying, storing or transporting the aromatic vinyl compound is one wherein a hydroxyl group and a nitro group bonded on the benzene ring are located in the ortho-position, as represented by the general formula (I), wherein A, B, C and D independently represent hydrogen, a nitro group, a carboxyl group, a hydroxyl group, or a straight or branched chain alkyl group having 1–12 carbon atoms. One or more of these 2-nitrophenol compounds may be used. The preferred examples of the 2-nitrophenol compound are 2,4-dinitrophenol, 2,6-dinitrophenol, 2,4-dinitro-6-methylphenol, 2,6-dinitro-4-methylphenol, 2,4-dinitro-6-sec-butylphenol and 2,6-dinitro-4-sec-butylphenol.

Also, the sulfonic acid compound of the (B) component which is added in combination with 2-nitrophenol of the (A) component is one represented by the general formula (II) wherein R represents a hydroxyl group, a straight or branched chain alkyl group having 1–32 carbon atoms, an alkylphenyl or an alkylnaphthyl group each having at least one straight or a branched chain alkyl group having 1–32 carbon atoms. One or more of these sulfonic acid compounds may be used. As a sulfonic acid compound, any one may be used so long as it is a so-called free sulfonic acid compound which is not in the form of a salt with an alkali metal such as sodium or potassium, with an alkaline earth metal such as calcium, with an amine or is not in the form of complex. As is apparent from the Examples and Comparative Examples described later, even when a sulfonic acid compound in the form of a salt was used in combination with a 2-nitrophenol compound, there could not be obtained the synergic effect as the present invention intended in the polymerization-inhibiting effect toward the aromatic vinyl compound. The compound which is capable of exerting the significant synergic effect in combination with the 2-nitrophenol compound is specified to the free sulfonic acid compound. This can be utterly unexpected from the prior art knowledge. Specific examples of a free sulfonic acid compound include sulfuric acid, toluenesulfonic acid, xylenesulfonic acid, cumenesulfonic acid, dodecylbenzenesulfonic acid, pentadecylbenzenesulfonic acid, dinonylnaphthalenesulfonic acid, and the like. Especially, pentadecylbenzenesulfonic acid and dodecylbenzenesulfonic acid are more preferred from the standpoint of view of dissolubility in the aromatic vinyl compound, cost and so on.

As stated above, the present invention comprises adding a 2-nitrophenol compound in combination with a sulfonic acid compound to the stage of producing, purifying, storing or transporting the aromatic vinyl compound. Although the mixture ratio of both the compounds may be optionally selected, the 2-nitrophenol compound and sulfonic acid compound are mixed in the range of 95:5–5:95, preferably 80:20–20:80, more preferably 70:30–30:70 ratio by weight to achieve the synergistic effect.

The amount of 2-nitrophenol compound and sulfonic acid compound to be added to said step may be varied depending on the condition of the step to be added, the extent required for polymerization inhibition and so on, and hence, it cannot be determined as a rule. However, the 2-nitrophenol compound is used in the range of usually 1–3,000 ppm, preferably 10–2,000 ppm, more preferably 100–1,000 ppm, based on the aromatic vinyl compound to be added while the sulfonic acid compound is similarly used in the range of 1–3,000 ppm, preferably 10–2,000 ppm, more preferably 100–1,000 ppm. These amounts added of the respective components are values found as the proper range to exert the polymerization-inhibiting effect toward the aromatic vinyl compound. When they are smaller than this range, the effect is not sufficient. Also, when they are greater than this range, the effect is sufficient but, in some cases, it does not become great relative to the added amount and it is not preferable from the economical aspect.

Although the place in said step where the 2-nitrophenol compound and sulfonic acid compound are added is not particularly restricted in the present invention, they are usually added to the upstream process over the place at which the aromatic vinyl compound undergoes polymerization to cause the problem as fouling. For example, styrene is generally manufactured by a dehydrogenation reaction of ethyl benzene, and the formed styrene is continuously separated from the unreacted ethyl benzene by distillation, and therefore it is recommendable that the 2-nitrophenol compound and sulfonic acid compound are supplied to the distillation column after the dehydrogenation reaction of ethyl benzene has been conducted.

Although the means for the addition of the 2-nitrophenol compound and sulfonic acid compound to said stage is not particularly restricted in the present invention, such a suitable means may be selected as they may be added to the specific place at one time or otherwise they may be separately added to some places in portions. In this case, although the 2-nitrophenol compound and sulfonic acid compound may be added separately, it is practically convenient that both the compounds are added in a proper mixture ratio and in a state dissolved in the same liquid as the process fluid, for example, in the case of being applied to styrene, in a state dissolved in ethyl benzene or crude styrene.

In the present invention, no limitation shall be lodged on that any other known polymerization inhibitor than 2-nitrophenol compound and sulfonic acid compound is used at the same time in the range not impairing the effect of the present invention.

THE BEST MODE FOR CARRYING OUT THE INVENTION

Figure 1:
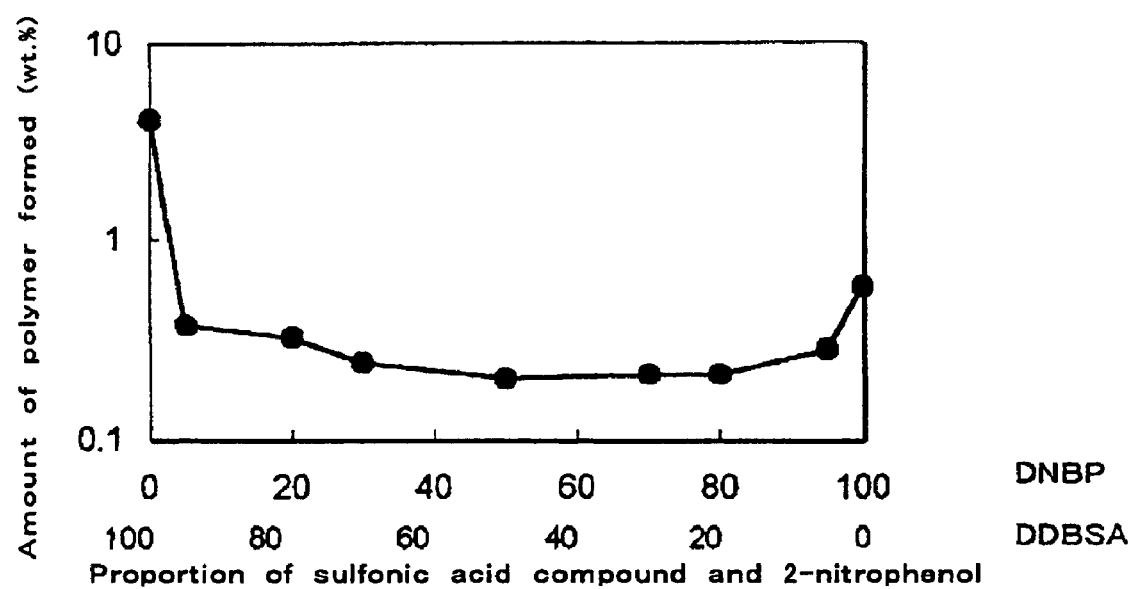
FIG. 1 indicates the relationship between the compounding ratio of dodecylbenzenesulfonic acid (DDBSA) and 2,4-dinitro-6-sec-butylphenol (DNBP) and the polymerization-inhibiting effect toward a styrene monomer (the amount of styrene polymer formed after a lapse of 120 minutes).

The present invention is further illustrated by the following Examples but it is not restricted thereto.

2-Nitrophenol Compounds
 DNBP: 2,4-dinitro-6-sec-butylphenol
 DNBP (2): 2,6-dinitro-4-sec-butylphenol
 DNP: 2,4-dinitrophenol
 DNP (2): 2,6-dinitrophenol
 DNOC: 2,4 dinitro-6-methylphenol
 DNOC (2): 2,6 dinitro-4-methylphenol Sulphonic Acid Compounds
 S: sulfuric acid (98%)
 MS: methanesulfonic acid
 PTS: p-toluenesulfonic acid
 XSA: xylenesulfonic acid
 CSA: cumenesulfonic acid
 DDBSA: dodecylbenzenesulfonic acid
 PDBSA: pentadecylbenzenesulfonic acid
 DNNSA: dinonylnaphthalenesulfonic acid Others
 BHT: 2,6-di-tert-butyl-4-toluene
 TBC: tert-butylcatechol
 NDPA: N-nitorosodiphenylamine
 NPH: p-nitrosophenol
 DEHA: diethylhydroxylamine
 DDBSA-Na: sodium dodecybenzenesulfonate
 DBSA-Ca: calcium dodecylbenzenesulfonate
 DDBSA-N: tetradecylamine dodecybenzenesulfonate Polymerization-inhibiting Test—1

100 Grams of styrene monomer was placed in a four-necked flask equipped with a reflux condenser, the prescribed amount of each of the polymerization inhibitors (shown in Table 1, where the compounding ratios of each chemical agent are also shown) was added thereto, and highly purified nitrogen gas was injected therein for 30 minutes to remove the dissolved oxygen. Then, the resultant mixture was kept at 110° C. and a part of the content therein was taken out as a sample to measure the amount of polymer formed in the liquid. Nine times the volume of methanol, based on the sampling liquid, was added to precipitate the polymer in a state suspended in the liquid, which was filtered out to determine its weight amount and its formed amount percent in the monomer was evaluated. Incidentally, before the beginning of this test, the styrene monomer was washed with an alkali to remove the polymerization inhibitor contained in the monomer, washed with water and dried. The obtained results are shown in Table 1.

TABLE 1

| | | Sulfonic acid Compounds Name of compound And amount added (ppm) | 2-Nitrophenol Compounds Name of compound And amount added (ppm) | Passage of time (min.) and Amount of polymer formed (wt. %) | | | |
|---|---|---|---|---|---|---|---|
| Ex. | No. | | | After 30 min. | After 60 min. | After 90 min. | After 120 min. |
| Example | 1 | DDBSA: 5 | DNBP: 95 | 0.05 | 0.10 | 0.19 | 0.28 |
| | 2 | DDBSA: 20 | DNBP: 80 | 0.03 | 0.09 | 0.14 | 0.21 |
| | 3 | DDBSA: 30 | DNBP: 70 | 0.03 | 0.09 | 0.14 | 0.21 |
| | 4 | DDBSA: 50 | DNBP: 50 | 0.03 | 0.09 | 0.14 | 0.20 |
| | 5 | DDBSA: 70 | DNBP: 30 | 0.04 | 0.11 | 0.17 | 0.24 |
| | 6 | DDBSA: 80 | DNBP: 20 | 0.06 | 0.14 | 0.23 | 0.32 |
| | 7 | DDBSA: 95 | DNBP: 5 | 0.06 | 0.14 | 0.26 | 0.37 |
| | 8 | DDBSA: 50 | DNBP (2): 50 | 0.03 | 0.09 | 0.15 | 0.21 |
| | 9 | DDBSA: 50 | DNP: 50 | 0.03 | 0.08 | 0.14 | 0.20 |
| | 10 | DDBSA: 50 | DNP (2): 50 | 0.03 | 0.09 | 0.15 | 0.21 |
| | 11 | DDBSA: 50 | DNOC: 50 | 0.03 | 0.09 | 0.15 | 0.21 |
| | 12 | DDBSA: 50 | DNOC (2): 50 | 0.03 | 0.09 | 0.15 | 0.22 |
| | 13 | S: 50 | DNBP: 50 | 0.04 | 0.05 | 0.07 | 0.10 |
| | 14 | MS: 50 | DNBP: 50 | 0.03 | 0.05 | 0.08 | 0.11 |
| | 15 | PTS: 50 | DNBP: 50 | 0.02 | 0.06 | 0.09 | 0.12 |
| | 16 | XSA: 50 | DNBP: 50 | 0.03 | 0.06 | 0.10 | 0.15 |
| | 17 | CSA: 50 | DNBP: 50 | 0.03 | 0.07 | 0.11 | 0.15 |
| | 18 | PDBSA: 50 | DNBP: 50 | 0.02 | 0.06 | 0.13 | 0.21 |
| | 19 | DNNSA: 50 | DNBP: 50 | 0.03 | 0.06 | 0.13 | 0.21 |
| Comparative Example | 1 | Nothing | Nothing | 2.73 | 5.43 | >10 | >10 |
| | 2 | DDBSA: 100 | Nothing | 1.02 | 2.03 | 3.02 | 4.03 |
| | 3 | PTS: 100 | Nothing | 1.20 | 2.40 | 3.49 | 4.58 |
| | 4 | XSA: 100 | Nothing | 1.22 | 2.12 | 3.51 | 4.80 |
| | 5 | CSA: 100 | Nothing | 1.01 | 2.21 | 3.61 | 5.00 |
| | 6 | PDBSA: 100 | Nothing | 1.10 | 2.31 | 3.70 | 5.00 |
| | 7 | DNNSA: 100 | Nothing | 1.09 | 2.39 | 3.80 | 5.24 |
| | 8 | Nothing | DNBP: 100 | 0.08 | 0.22 | 0.39 | 0.58 |
| | 9 | Nothing | DNBP (2): 100 | 0.08 | 0.23 | 0.40 | 0.60 |
| | 10 | Nothing | DNP: 100 | 0.06 | 0.16 | 0.28 | 0.42 |
| | 11 | Nothing | DNP (2): 100 | 0.06 | 0.17 | 0.30 | 0.45 |

TABLE 1-continued

| Ex. | No. | Sulfonic acid Compounds Name of compound And amount added (ppm) | 2-Nitrophenol Compounds Name of compound And amount added (ppm) | Passage of time (min.) and Amount of polymer formed (wt. %) | | | |
|---|---|---|---|---|---|---|---|
| | | | | After 30 min. | After 60 min. | After 90 min. | After 120 min. |
| | 12 | Nothing | DNOC: 100 | 0.08 | 0.21 | 0.39 | 0.61 |
| | 13 | Nothing | DNOC (2): 100 | 0.08 | 0.22 | 0.40 | 0.63 |
| | 14 | DDBSA: 50 | BHT: 50 | 2.78 | 5.48 | >10 | >10 |
| | 15 | DDBSA: 50 | TBC: 50 | 2.69 | 5.45 | >10 | >10 |
| | 16 | DDBSA: 50 | NDPA: 50 | 0.30 | 6.49 | >10 | >10 |
| | 17 | DDBSA: 50 | NPH: 50 | 0.28 | 6.98 | >10 | >10 |
| | 18 | DDBSA: 50 | DEHA: 50 | 0.20 | 6.66 | >10 | >10 |
| | 19 | DDBSA-Na: 50 | DNBP: 50 | 0.15 | 0.41 | 0.65 | 1.23 |
| | 20 | DDBSA-Ca: 50 | DNBP: 50 | 0.16 | 0.41 | 0.64 | 1.20 |
| | 21 | DDBSA-N: 50 | DNBP: 50 | 0.15 | 0.41 | 0.63 | 1.22 |

It can be understood from the results shown in Table 1 that by combining the sulfonic acid compound and the 2-nitrophenol compound, each of them showing almost no appreciable polymerization-inhibiting effect when used singly, a synergistic effect may be exerted and the polymerization-inhibiting effect is maintained over a long period of time. Whereas, as shown by Comparative Examples 14–18, when other polymerization inhibitors (BHT, TBC, NDPA, NPH and DEHA) than the 2-nitrophenol compound were used, no synergistic effect may be exerted. Also, as shown by Comparative Examples 19–21, even when the 2-nitrophenol compound was combined with salts of sulfonic acid, no synergistic effect was exerted, too. Thus, only by the combination of the sulfonic acid compound and the 2-nitrophenol compound involved in the present invention, a high polymerization-inhibiting effect may be exerted.

The relationship between the compounding ratios of DDBSA and DNBP (total amount added: 100 ppm) and the amount of polymer formed after a lapse of 120 minutes is indicated in FIG. 1. As is apparent from FIG. 1, it is extremely surprising that merely by combining a small amount of a 2-nitrophenol compound with a sulfonic acid compound, which shows almost no polymerization-inhibiting effect when used singly, an excellent polymerization-inhibiting effect is realized than when 2-nitrophenol was used singly.

Polymerization-inhibiting Test—2

A polymerization-inhibiting test was carried out in a similar manner as in polymerization-inhibiting test-1 except that methylstyrene was used in place of the styrene monomer. The obtained results are in Table 2.

TABLE 2

| Ex. | | No. | Sulfonic acids Name of compound And amount added (ppm) | 2-Nitrophenols Name of compound And amount added (ppm) | Passage of time (min.) and Amount of polymer formed (wt. %) | | | |
|---|---|---|---|---|---|---|---|---|
| | | | | | After 30 min. | After 60 min. | After 90 min. | After 120 min. |
| Example | | 20 | DDBSA: 95 | DNBP: 5 | 0.08 | 0.19 | 0.34 | 0.52 |
| | | 21 | DDBSA: 50 | DNBP: 50 | 0.07 | 0.17 | 0.29 | 0.42 |
| | | 22 | DDBSA: 5 | DNBP: 95 | 0.09 | 0.21 | 0.35 | 0.50 |
| | | 23 | DDBSA: 95 | DNBP (2): 5 | 0.08 | 0.20 | 0.35 | 0.51 |
| | | 24 | DDBSA: 50 | DNBP (2): 5 | 0.06 | 0.16 | 0.29 | 0.41 |
| | | 25 | DDBSA: 5 | DNBP (2): 5 | 0.09 | 0.22 | 0.34 | 0.52 |
| Comparative | | 22 | Nothing | Nothing | 3.03 | 6.15 | >10 | >10 |
| Example | | 23 | DDBSA: 100 | Nothing | 2.22 | 5.10 | >10 | >10 |
| | | 24 | Nothing | DNBP: 100 | 0.13 | 0.30 | 0.52 | 0.80 |
| | | 25 | Nothing | DNBP (2): 100 | 0.12 | 0.31 | 0.50 | 0.83 |

It can be understood that the polymerization-inhibiting effect caused by the combination of the sulfonic acid compound and the 2-nitrophenol compound in the present invention is not dependent on the kind of substituent R in the sulfonic acid compound but dependent on the content of the sulfonic acid radical in the sulfonic acid compound (number of sulfonic acid radical/molecular weight of sulfonic acid compound) and that the higher the content of the sulfonic acid radical in the sulfonic acid compound, the greater the polymerization-inhibiting effect.

It can be understood from the results shown in Table 2 that by the addition of a 2-nitrophenol compound in combination with a sulfonic acid compound, a synergistic effect is recognized and the polymerization inhibition against methylstyrene is maintained over a long period of time.

Polymerization-inhibiting Test—3

A polymerization-inhibiting test was carried out in a similar manner as in polymerization-inhibiting test-1 except that divinylbenzene was used in place of the styrene monomer. The obtained results are in Table 3.

TABLE 3

| Ex. | No. | Sulfonic acids Name of compound And amount added (ppm) | 2-Nitrophenols Name of compound And amount added (ppm) | Passage of time (min.) and Amount of polymer formed (wt. %) | | | |
|---|---|---|---|---|---|---|---|
| | | | | After 30 min. | After 60 min. | After 90 min. | After 120 min. |
| Example | 26 | DDBSA: 95 | DNBP: 5 | 0.13 | 0.29 | 0.54 | 0.84 |
| | 27 | DDBSA: 50 | DNBP: 50 | 0.12 | 0.29 | 0.48 | 0.68 |
| | 28 | DDBSA: 5 | DNBP: 95 | 0.13 | 0.31 | 0.53 | 0.78 |
| | 29 | DDBSA: 95 | DNBP (2): 5 | 0.11 | 0.29 | 0.55 | 0.88 |
| | 30 | DDBSA: 50 | DNBP (2): 50 | 0.10 | 0.27 | 0.49 | 0.64 |
| | 31 | DDBSA: 5 | DNBP (2): 95 | 0.13 | 0.32 | 0.53 | 0.75 |
| Comparative Example | 26 | Nothing | Nothing | 3.45 | 6.30 | >10 | >10 |
| | 27 | DDBSA: 100 | Nothing | 2.01 | 4.38 | >10 | >10 |
| | 28 | Nothing | DNBP: 100 | 0.2 | 0.44 | 0.7 | 1.05 |
| | 29 | Nothing | DNBP (2): 100 | 0.19 | 0.43 | 0.75 | 1.03 |

Polymerization-inhibiting Test—4

To 30 g of the bottom liquid (containing above 90% by weight of styrene) in the distillation column of a styrene production apparatus were added a sulfonic acid compound and a 2-nitrophenol compound in the present invention or otherwise were added another polymerization inhibitor and a salt of sulfonic acid as comparative examples and, in either case, the resultant mixture was allowed to settle in a 100 ml pressure glass autoclave at 100° C. for 2 hours. The formed insoluble matters were filtered out, washed with acetone and dried at 105° C. or 2 hours to measure its weight amount. Also, the state of the insoluble matters adhered to the inner walls of the autoclave was observed. The state of adhesion was visually evaluated according to the following criteria:

A: no adhesion is recognized.

B: slight adhesion is recognized.

C: adhesion is recognized.

D: adhesion of a large amount is recognized.

The obtained results are shown in Table 4.

TABLE 4

| | | Sulfonic acid Compound Compound and Amount added (ppm) | 2-Nitrophenols And Polymerization Inhibitors Compound and Amount added (ppm) | Effect | |
|---|---|---|---|---|---|
| | | | | Amount of Insoluble Matters formed (mg/kg) | Adhesion State of Insoluble Matters |
| Example | 26 | DDBSA: 100 | DNBP: 100 | 5 | A |
| | 27 | DDBSA: 200 | DNBP: 100 | 2 | A |
| | 28 | DDBSA: 500 | DNBP: 100 | 1 | A |
| | 29 | DDBSA: 1000 | DNBP: 100 | 0 | A |
| | 30 | DDBSA: 100 | DNBP (2): 100 | 6 | A |
| | 31 | DDBSA: 200 | DNBP (2): 100 | 2 | A |
| | 32 | DDBSA: 500 | DNBP (2): 100 | 1 | A |
| | 33 | DDBSA: 1000 | DNBP (2): 100 | 0 | A |
| Comparative Example | 30 | DDBSA: 100 | Nothing | 135 | D |
| | 31 | DDBSA: 1000 | Nothing | 131 | C |
| | 32 | Nothing | DNBP: 100 | 140 | C |
| | 33 | Nothing | DNBP (2): 100 | 143 | C |
| | 34 | DDBSA-Na: 1000 | Nothing | 123 | B |
| | 35 | DDBSA-Na: 100 | DNBP: 100 | 41 | A |
| | 36 | DDBSA-Na: 100 | DNBP (2): 100 | 40 | A |
| | 37 | DDBSA-Ca: 1000 | Nothing | 134 | D |
| | 38 | DDBSA-Ca: 1000 | DNBP: 100 | 42 | A |
| | 39 | DDBSA-Ca: 100 | DNBP (2): 100 | 41 | A |
| | 40 | DDBSA-N: 1000 | Nothing | 118 | B |
| | 41 | DDBSA-N: 1000 | DNBP: 100 | 41 | A |
| | 42 | DDBSA-N: 100 | DNBP (2): 100 | 41 | A |
| | 43 | DDBSA: 1000 | NPH: 100 | 40 | A |
| | 44 | Nothing | NPH: 100 | 132 | D |
| | 45 | DDBSA-Na: 100 | NPH: 100 | 44 | A |
| | 46 | DDBSA-Ca: 1000 | NPH: 100 | 90 | A |
| | 47 | DDBSA-N: 1000 | NPH: 100 | 35 | A |

As is apparent from Table 4, with respect to the polymerization-inhibiting effect caused by the combination of the sulfonic acid compound and the 2-nitrophenol compound involved in the present invention, the effect is exerted in the case where the sulfonic acid compound is in the free form of sulfonic acid while the effect of the present invention cannot be achieved in the case where the sulfonic acid compound is in the form of a metal salt such as sodium, calcium or the like salt and of an amine salt.

INDUSTRIAL APPLICABILITY

The 2-nitrophenol compound is added in combination with the free sulfonic acid compound to the stage of producing, purifying, storing or transporting an aromatic vinyl compound, whereby the polymerization of an aromatic vinyl compound or of a process fluid containing it may be efficiently inhibited and the effect may be maintained for a long period of time thereby minimizing the amount of fouling generated in the facilities involved and attributing greatly to a smooth and long-term operation without causing any trouble in operating the facilities.

The invention claimed is:

1. A process for inhibiting polymerization of an aromatic vinyl compound which is characterized by adding (A) 2-nitrophenol compound represented by the general formula (I) together with (B) sulfonic acid compound represented by the general formula (II) to the aromatic vinyl compound during the stage of producing, purifying, storing or transporting the aromatic vinyl compound

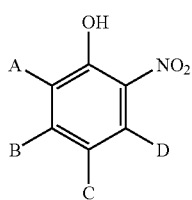

(I)

wherein A, B, C and D independently represent hydrogen, a nitro group, a carboxyl group, a hydroxyl group, or a straight or branched chain alkyl group having 1–12 carbon atoms,

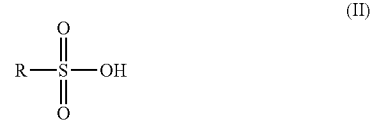

(II)

wherein R represents a hydroxyl group, a straight or branched chain alkyl group having 1–32 carbon atoms, an alkyl phenyl or an alkyl naphthyl group, each having at least one straight or branched chain alkyl group having 1–32 carbon atoms.

2. The process for inhibiting polymerization of an aromatic vinyl compound as claimed in claim 1, wherein the 2-nitrophenol compound represented by the general formula (I) is at least one member selected from the group consisting of 2,4-dinitrophenol, 2,6-dinitrophenol, 2,4-dinitro-6-methylphenol, 2,6-dinitro-4-methylphenol, 2,4-dinitro-6-sec-butylphenol and 2,6-dinitro-4-sec-butylphenol.

3. The process for inhibiting polymerization of an aromatic vinyl compound as claimed in claim 1, wherein the sulfonic acid compound represented by the general formula (II) is at least one member selected from the group consisting of sulfuric acid, toluenesulfonic acid, xylenesulfonic acid, cumenesulfonic acid, dodecylbenzenesulfonic acid, pentadecylbenzenesulfonic acid and dinonylnaphthalenesulfonic acid.

4. The process for inhibiting polymerization of an aromatic vinyl compound as claimed in claim 1, wherein the (A) 2-nitrophenol compound and (B) sulfonic acid compound are added in combination in a proportion of 5:95–95:5 in weight ratio.

5. The process for inhibiting polymerization of an aromatic vinyl compound as claimed in claim 1, wherein the 2-nitrophenol compound is at least one member selected from the group consisting of 2,4-dinitro-6-sec-butylphenol, 2,6-dinitro-4-sec-butylphenol, 2,4-dinitrophenol, 2,6-dinitrophenol, 2,4-dinitro-6-methylphenol and 2,6-dinitro-4-methylphenol and the sulfonic acid compound is at least one member selected from the group consisting of sulfuric acid, methanesulfonic acid, p-toluenesulfonic acid, xylenesulfonic acid, cumenesulfonic acid, dodecylbenzenesulfonic acid, pentadecylbenzenesulfonic acid and dinonylnaphthalenesulfonic acid.

* * * * *